(12) United States Patent
Frey et al.

(10) Patent No.: US 9,018,417 B2
(45) Date of Patent: Apr. 28, 2015

(54) PROCESS FOR RECOVERING ALIPHATIC MONOCARBOXYLIC ACIDS FROM DISTILLATION

(71) Applicant: Oxea GmbH, Oberhausen (DE)

(72) Inventors: Guido D. Frey, Riedstadt (DE); Jörg Arnold, Dinslaken (DE); Wolfgang Höfs, Oberhausen (DE); Matthias Kramer, Bottrop-Grafenwald (DE); Thomas Müller, Dinslaken (DE); Heinz Strutz, Moers (DE)

(73) Assignee: Oxea GmbH, Oberhausen (DE)

( * ) Notice: Subject to any disclaimer, the term of this patent is extended or adjusted under 35 U.S.C. 154(b) by 0 days.

(21) Appl. No.: 14/358,239

(22) PCT Filed: Nov. 20, 2012

(86) PCT No.: PCT/EP2012/004809
§ 371 (c)(1),
(2) Date: May 15, 2014

(87) PCT Pub. No.: WO2013/083236
PCT Pub. Date: Jun. 13, 2013

(65) Prior Publication Data
US 2014/0303401 A1  Oct. 9, 2014

(30) Foreign Application Priority Data

Dec. 8, 2011 (DE) .............. 10 2011 120 587 U

(51) Int. Cl.
C07C 51/50 (2006.01)
C07C 51/02 (2006.01)
C07C 51/235 (2006.01)
C07C 51/44 (2006.01)
C07C 51/48 (2006.01)

(52) U.S. Cl.
CPC .............. C07C 51/50 (2013.01); C07C 51/02 (2013.01); C07C 51/235 (2013.01); C07C 51/44 (2013.01); C07C 51/48 (2013.01)

(58) Field of Classification Search
CPC ....................................... C07C 51/50
USPC ....................................... 562/608
See application file for complete search history.

(56) References Cited

U.S. PATENT DOCUMENTS

| | | | |
|---|---|---|---|
| 5,504,229 A * | 4/1996 | Fisher et al. | 554/134 |
| 6,800,783 B2 | 10/2004 | Springer et al. | |
| 7,138,544 B2 | 11/2006 | Springer et al. | |
| 7,799,945 B2 | 9/2010 | Springer | |

FOREIGN PATENT DOCUMENTS

| | | |
|---|---|---|
| DE | 950007 C | 10/1956 |
| DE | 2460784 B1 | 4/1976 |
| DE | 10010771 C1 | 5/2001 |
| DE | 102004055252 A1 | 5/2006 |
| DE | 102006022168 A1 | 11/2007 |
| FR | 2769624 A1 | 4/1999 |
| JP | 53105413 | 9/1978 |

OTHER PUBLICATIONS

International Search Report dated Mar. 4, 2013.
Ullmanns Encyclopädie der technischen Chemie, 4th edition 1975 vol. 9, p. 139.

* cited by examiner

*Primary Examiner* — Yong Chu
(74) *Attorney, Agent, or Firm* — Michael W. Ferrell

(57) ABSTRACT

A process is provided for recovering aliphatic monocarboxylic acids having from 4 to 11 carbon atoms from the distillation residue obtained in the oxidation of the corresponding aldehyde by means of oxygen or oxygen-containing gas mixtures in the presence of alkali metal carboxylates or alkaline earth metal carboxylates to form the corresponding monocarboxylic acid and subsequent distillation, characterized in that the distillation residue is reacted with an aqueous acid in a tube reactor and the two-phase mixture flowing out from the tube reactor is introduced into a settling vessel in which the organic phase which separates out has a pH of 4.5 or less.

20 Claims, 1 Drawing Sheet

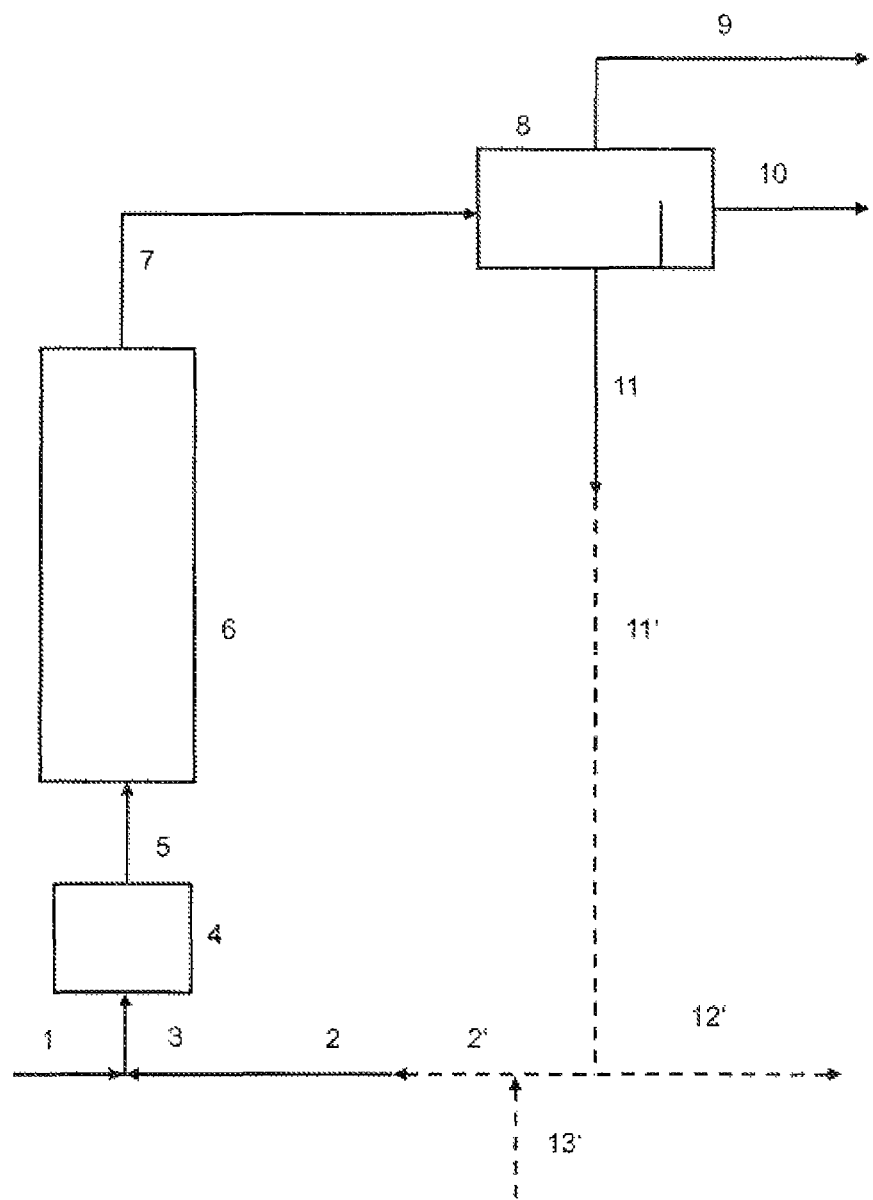

PROCESS FOR RECOVERING ALIPHATIC MONOCARBOXYLIC ACIDS FROM DISTILLATION

CLAIM FOR PRIORITY

This application is a national phase application of PCT/EP2012/004809 FILED Nov. 20, 2012 which was based on application DE 10 2011 120 587.3 FILED Dec. 8, 2011. The priorities of PCT/EP2012/004809 and DE 10 2011 120 587.3 are hereby claimed and their disclosures incorporated herein by reference.

TECHNICAL FIELD

The present invention relates to a process for recovering aliphatic monocarboxylic acids from distillation residues by treating these residues with an aqueous acid in a tube reactor.

BACKGROUND

Aldehydes are the customary starting materials for obtaining carboxylic acids. The position of preference for this field of use is thanks to their availability in great variety and the ease of conversion of the carbonyl group into the carboxyl group by oxidation. In processes carried out industrially, the conversion of aldehydes into carboxylic acids is carried out either in the presence or in the absence of catalysts or additives. Possible catalysts are predominantly salts of transition metals, in particular salts of cobalt and of manganese and also of chromium, iron, copper, nickel, silver and vanadium. The formation of carboxylic acid from aldehydes is frequently associated with secondary reactions and degradation reactions even when optimal temperature conditions are adhered to. This applies equally for reactions in the presence and absence of catalysts. In such cases, the selectivity of the reaction can be improved considerably by use of alkali metal salts or alkaline earth metal salts of weak acids as additives (Ullmanns Encyclopadie der technischen Chemie, 4th edition 1975 volume 9, page 139).

Particularly in the oxidation of aliphatic, α-alkyl-branched aldehydes in which the carbon atom adjacent to the carbonyl carbon bears the alkyl branch, the prior art recommends the addition of small amounts of alkali metal carboxylates to improve the selectivity. Thus, for example, it is known from DE 950 007 that the oxidation of aldehydes branched in the a position requires the addition of small amounts of alkali metal salts of carboxylic acids in order to obtain the desired carboxylic acid in high yield and also high purity. It is known from U.S. Pat. No. 5,504,229 that the alkali metal-containing distillation residue obtained in the distillation of α-alkyl-branched carboxylic acids can be reused for the aldehyde oxidation. It is also stated that the α-alkyl-branched carboxylic acid can be liberated from the distillation residue by acidification. However, the subsequently purified carboxylic acid displays only a moderate colour number.

According to the teaching of the published Japanese patent application 53-105413, aliphatic, α-branched aldehydes are oxidized by means of oxygen in the presence of lithium compounds or alkaline earth metal compounds which are used in amounts of from 0.01 to 10% by weight, based on the total reaction system, in order to prepare aliphatic, α-branched carboxylic acids. The low-temperature oxidation process described in the French patent application 2 769 624 is also carried out in the presence of alkali metal compounds or alkaline earth metal compounds as additives. DE-C1-100 10 771 discloses both the sole use of alkali metal salts and the use of these in admixture with transition metals in the oxidation of 2-methylbutanal.

In the oxidation of aliphatic straight-chain or branched aldehydes which do not bear an alkyl branch in the α position, too, the use of a mixture of alkali metal carboxylates or alkaline earth metal carboxylates with transition metals has been described. DE 10 2004 055 252 A1 discloses the oxidation of n-pentanal or of isononanal based on 3,5,5-trimethylhexanal in the presence of the corresponding potassium carboxylate and iron. The crude acid obtained after oxidation is separated off by distillation and the metal-containing distillation residue obtained can be reused in the aldehyde oxidation. According to the teaching of DE 10 2006 022 168 A1, a mixture of alkali metal carboxylates or alkaline earth metal carboxylates and transition metals is prepared as reaction product in a first aldehyde oxidation reaction and this reaction product is reused for the subsequent oxidation of aliphatic straight-chain or β-alkyl-branched monocarboxylic acids.

It is usual for the respective carboxylic acid firstly to be reacted in a separate reaction with an aqueous solution of an alkali metal compound or alkaline earth metal compound, preferably with an aqueous alkali metal hydroxide or alkaline earth metal hydroxide solution, to convert it into the respective carboxylate which is mixed into the aldehyde to be oxidized. An aqueous alkali metal hydroxide or alkaline earth metal hydroxide solution can also be added to the reaction mixture so that the formation of the respective carboxylates occurs during the oxidation. The use of potassium carboxylates has been found to be particularly useful. After the oxidation reaction is complete, the crude acid is worked up by distillation, giving a highly viscous distillation residue containing alkali metal carboxylate or alkaline earth metal carboxylate. This distillation residue can to a certain extent be recirculated to the oxidation process.

However, as the amount recirculated increases, the selectivity of the aldehyde oxidation decreases and the distillation residue ultimately has to be discharged from the process.

SUMMARY OF INVENTION

However, since the highly viscous distillation residue contains not only high boilers but a predominant proportion of the desired aliphatic monocarboxylic acid, either in the form of the carboxylate or as physically mixed-in free aliphatic monocarboxylic acid, it is desirable to recover the aliphatic monocarboxylic acid in a simple way from the residues of monocarboxylic acid distillation and thus improve the productivity and therefore the economics of the oxidation process. The amount of highly viscous distillation residue obtained should also be decreased in order to reduce the outlay for disposal.

The present invention accordingly provides a process for recovering aliphatic monocarboxylic acids having from 4 to 11 carbon atoms from the distillation residue obtained in the oxidation of the corresponding aldehyde by means of oxygen or oxygen-containing gas mixtures in the presence of alkali metal carboxylates or alkaline earth metal carboxylates to form the corresponding monocarboxylic acid and subsequent distillation, characterized in that the distillation residue is brought into contact with an aqueous acid in a tube reactor and the two-phase mixture flowing out from the tube reactor is introduced into a settling vessel in which the organic phase which separates out has a pH of 4.5 or less.

BRIEF DESCRIPTION OF DRAWING

The invention is described in detail below with reference to FIG. 1 which is a schematic diagram illustrating the process and an illustrative system for practicing the present invention.

DETAILED DESCRIPTION

The two-phase mixture of the treated organic distillation residue and the aqueous acid present after leaving the tube reactor surprisingly separates without problems into the liquid organic phase and aqueous phase in a downstream settling vessel. The phase separation occurs spontaneously and sharply without formation of a foam-like intermediate layer. Such an advantageous sharp phase separation was not to be expected since, due to the surface-active properties of the alkali metal carboxylates or alkaline earth metal carboxylates, foam formation could have been expected on contact with the aqueous phase. The rapid and sharp phase separation firstly makes a high throughput of the organic distillation residue and the aqueous acid possible. Furthermore, contamination of the aqueous phase with organic constituents after phase separation remains limited and the alkali metal or alkaline earth metal content of the organic phase can be reduced to an acceptable level.

As starting material, use is made of the alkali metal- or alkaline earth metal-containing residue from the distillation of aliphatic monocarboxylic acids having from 4 to 11 carbon atoms which are prepared by oxidation of the corresponding aldehydes by means of oxygen or oxygen-containing gas mixtures in the presence of alkali metal carboxylates or alkaline earth metal carboxylates. The alkali metal carboxylates or alkaline earth metal carboxylates are the carboxylates of, for example, lithium, sodium or potassium or of calcium or barium. The aldehyde oxidation is preferably carried out in the presence of the corresponding potassium carboxylate. In general, a solution containing alkali metal carboxylate or alkaline earth metal carboxylate is prepared by neutralizing an aqueous solution containing the alkali metal compound or alkaline earth metal compound with an excess of the desired carboxylic acid and the solution is added to the aliphatic aldehyde to be oxidized. Alkali metal compounds or alkaline earth metal compounds which are suitable for this purpose are, in particular, the hydroxides, carbonates or hydrogencarbonates. However, it is also possible to generate the alkali metal carboxylates or alkaline earth metal carboxylates in the reaction mixture by adding alkali metal compounds or alkaline earth metal compounds which are converted under the reaction conditions into the carboxylates to the reaction mixture. For example, it is possible to use alkali metal or alkaline earth metal hydroxides, carbonates, hydrogencarbonates or oxides. They can be added either in solid form or as aqueous solution.

The alkali metal or alkaline earth metal contents of the distillation residue to be worked up is generally in the range from 3 to 15% by weight, preferably from 5 to 10% by weight, based on the total distillation residue. Apart from the appropriately bound carboxylate, the distillation residue also contains free aliphatic monocarboxylic acid in an amount which depends on the distillation conditions. The organic part of the distillation residue comprises, depending on the distillation conditions, up to 98% by weight of the respective aliphatic monocarboxylic acid in the form of free aliphatic monocarboxylic acid and the corresponding carboxylate. The balance to 100% in the organic part contains predominantly oxygen-containing high boilers. The composition indicated can be considered to be a guideline value and can be varied by means of the distillation conditions, for example the degree of thickening. However, an excessively high degree of concentration is to be avoided since otherwise the distillation residue to be worked up has an excessive viscosity and can no longer be pumped satisfactorily. Owing to the highly viscous consistency, it is advisable to preheat the distillation residue to a temperature of from 30 to 90° C., preferably from 50 to 80° C., before introduction into the tube reactor.

The distillation residue to be worked up is brought into contact with an aqueous acid in the tube reactor. Here, the organic and aqueous streams can be introduced separately but simultaneously into the tube reactor. The two liquids are preferably mixed beforehand and introduced as two-phase mixture of organic phase and aqueous phase into the tube reactor. In a particularly preferred embodiment, the two-phase mixture is conveyed through an upstream static mixing element in order to intensify contact between the two phases before entry into the tube reactor. Such mixing elements are commercially available and are offered, for example, as Sulzer mixers or Kenicks mixers with specific product lines for the mixing of liquids having different viscosities.

The distillation residue to be worked up and the aqueous acid can be introduced separately or as a mixture into the tube reactor. In the case of separate addition, organic and aqueous phases can flow into the tube reactor either in cocurrent or in countercurrent. A suitable tube reactor is, for example, a flow tube having any desired arrangement, for example a vertical or horizontal flow tube or a simply coiled flow tube. The tube reactor can likewise contain packing elements or internals, for example Raschig ring, saddles, Pall rings, helices, baffles or static mixers or mixer packings. The reactor is preferably operated continuously.

As aqueous acid, use is made of aqueous solutions of inorganic acids which have a sufficient acid strength in order to convert the alkali metal carboxylates or alkaline earth metal carboxylates present in the distillation residue to be worked up into the corresponding aliphatic monocarboxylic acids. Suitable inorganic acids are, for example, hydrochloric acid, sulphuric acid, phosphoric acid or nitric acid which are used as aqueous solution having an acid content of from 1 to 20% by weight, preferably from 5 to 10% by weight. An aqueous 5-10% strength by weight sulphuric acid solution has been found to be particularly useful. The aqueous acid is used in such an amount that a from 1 to 20%, preferably 10%, equivalent excess, based on the amount of acid required for complete conversion, is present per equivalent of alkali metal carboxylate or alkaline earth metal carboxylate. The conversion or liberation of the aliphatic monocarboxylic acid is, owing to the high viscosity of the distillation residue, preferably carried out at a temperature of from 30 to 90° C., in particular from 50 to 80° C., under autogenous pressure or slightly superatmospheric pressure, although the use of higher pressures, for example up to 0.8 MPa, is not ruled out.

A space velocity V/Vh of the distillation bottoms to be worked up through the tube reactor of from 0.1 to 10 h$^{-1}$ and a corresponding space velocity of the aqueous acid fed in of from 0.5 to 25 h$^{-1}$, in each case based on the reactor volume and time, has been found to be advantageous when the two streams are fed separately but simultaneously into the tube reactor. If the distillation bottoms and the aqueous acid are mixed beforehand, preferably by means of a static mixing element located upstream of the tube reactor, the heterogeneous two-phase mixture is introduced into the tube reactor at a space velocity of from 0.5 to 35 h$^{-1}$ based on the reactor volume and time. The space velocity can be varied over a wide range and even at high space velocities through the reactor in the range from 20 to 32 h$^{-1}$, satisfactory liberation of the desired aliphatic monocarboxylic acid and accordingly a reduction in the alkali metal or alkaline earth metal content of the organic phase is observed.

The two-phase mixture flowing out from the tube reactor is introduced into a settling vessel in which the aqueous phase separates spontaneously from the organic phase. The phase separation is sharp and without formation of a foam-like intermediate layer. The pH determined in the organic phase correlates with the residual content of alkali metal or alkaline earth metal and has 4.5 pH units or less. Within this pH range, a sufficiently low alkali metal or alkaline earth metal content of less than 1000 ppm in the organic phase is ensured. Should the pH of the organic phase be above 4.5, the reaction conditions, e.g. the amount and concentration of acid used and the space velocity of the aqueous acid through the tube reactor have to be varied so that the organic phase after phase separation has a pH of 4.5 or less. The correlation found between the pH in the organic phase and the alkali metal or alkaline earth metal content allows simple monitoring of the conversion process since pH values can be monitored very simply by measurement even in the ongoing process. The upper organic phase consists essentially of the aliphatic monocarboxylic acid which is liberated by the conversion and is worked up further in downstream distillation apparatuses. To avoid decomposition processes and the formation of colour-imparting components in the subsequent purification by distillation, a residual content of alkali metal salts or alkaline earth metal salts of less than 1000 ppm is advisable.

The aqueous solution obtained in the settling vessel contains the alkali metal salt or alkaline earth metal salt of the corresponding inorganic acid and the inorganic acid added in excess for the conversion. The aqueous phase, which has a pH in the range from 0.2 to 1.8, is removed from the process as wastewater and can be extracted with a polar organic solvent, for example with alcohols, esters or ethers, to reduce the content of organic impurities. However, it is also possible to recirculate the separated-off aqueous phase to the tube reactor with addition of fresh acid solution.

The aliphatic monocarboxylic acids having from 4 to 11 carbon atoms recovered from distillation residues by the process of the invention are obtained by oxidation of the corresponding $C_4$-$C_{11}$-aldehydes by means of oxygen or oxygen-containing gases. The origin of the aldehydes is not restricted to particular production processes. Owing to their ready availability, aldehydes obtained by means of the oxo process, i.e. by reaction of $C_3$-$C_{10}$-olefins with carbon monoxide and hydrogen, are preferred. In this context, it is not critical which specific embodiment of the oxo process has been employed for obtaining the aldehydes, i.e. whether the reaction has been catalysed, for example, by means of cobalt or by means of rhodium, whether the metals were used alone or together with complexing agents and whether the catalyst was homogeneously dissolved in the reaction mixture or formed a separate, heterogeneous phase. The process of the invention is suitable for aliphatic straight-chain or branched monocarboxylic acids.

The process of the invention is particularly suitable for recovering aliphatic, α-alkyl-branched monocarboxylic acids having from 4 to 11 carbon atoms, since the oxidation is usually carried out in the presence of alkali metal carboxylates or alkaline earth metal carboxylates to improve the selectivity. In particular, isobutyric acid, 2-ethylbutyric acid, 2-methylbutyric acid, 2-methylpentanoic acid, 2-methylhexanoic acid, 2-ethylhexanoic acid, 2-methyl-octanoic acid, 2-methylnonanoic acid and 2-propyl-heptanoic acid can be recovered from the distillation residues. However, the process of the invention can also be employed successfully for recovering straight-chain aliphatic monocarboxylic acids or aliphatic monocarboxylic acids having any branching other than α-alkyl branching as long as the aldehyde oxidation is carried out in the presence of alkali metal carboxylates or alkaline earth metal carboxylates. For example, n-butyric acid, n-pentanoic acid, n-hexanoic acid, n-heptanoic acid, n-octanoic acid, n-nonanoic acid, n-decanoic acid, isopentanoic acid having any branching, isohexanoic acid having any branching, isoheptanoic acid having any branching, isooctanoic acid having any branching, isononanoic acid having any branching, isodecanoic acid having any branching or isoundecanoic acid having any branching can be recovered by the process of the invention. As an example of isononanoic acid having any branching, isononanoic acid having the main constituent 3,5,5-trimethylhexanoic acid with the CAS number 3302-10-1, the corresponding aldehyde of which can be obtained by the oxo process using diisobutylene as starting material, can be recovered particularly advantageously. As isopentanoic acid having any branching, 3-methylbutyric acid can be recovered. The process of the invention can likewise be extended to the recovery of unsaturated, aliphatic monocarboxylic acids, for example unsaturated aliphatic, α-alkyl-branched monocarboxylic acids such as 2-ethylbutenoic acid, 2-methylpentenoic acid, 2-ethylhexenoic acid and 2-propylheptenoic acid, although the work-up of distillation residues from the preparation of these types of monocarboxylic acids tends to remain restricted to special cases.

The isolation of the desired aliphatic monocarboxylic acid from the distillation residues containing alkali metal or alkaline earth metal enables the economics of the overall process for preparing aliphatic monocarboxylic acids and their yields to be significantly improved.

The process of the invention will be illustrated below with the aid of the in-principle scheme as per FIG. 1. However, the process of the invention is not restricted to the embodiment shown in the drawing.

The alkali metal- or alkaline earth metal-containing residue from the distillation of aliphatic monocarboxylic acids, which has been heated to 50-80° C., is supplied via line (1) and a dilute aqueous solution of an inorganic acid is supplied via line (2) and the two are, after being combined in line (3), intensively mixed in the static mixer (4). The two-phase mixture subsequently enters the bottom of the tube reactor (6) via line (5). At the top of the reactor, the liquid reactor output is discharged via line (7) and introduced into a settling vessel (8) in which the lighter organic phase separates from the heavier aqueous phase. Gaseous components are discharged via line (9). The settled-out organic phase, which contains the desired aliphatic monocarboxylic acid, leaves the settling vessel (8) via line (10) and is distilled to give the pure acid in subsequent distillation steps (not shown in FIG. 1). The aqueous solution obtained in the settling vessel (8) contains the alkali metal salt or alkaline earth metal salt of the inorganic acid added and is discharged via line (11). To reduce the proportion of organic material, the aqueous phase can be extracted with a polar organic solvent, for example with an organic alcohol such as 2-ethylhexanol.

In a further embodiment, the aqueous solution discharged via line (11) can be recirculated via line (11') and via line (2') to the process, optionally after removal of a substream via line (12') and addition of fresh acid via line (13').

The process of the invention is illustrated below with the aid of a few examples but is not restricted to the embodiments described.

EXAMPLES

Recovery of 2-ethylhexanoic Acid

A potassium-containing distillation residue from the oxidation of 2-ethylhexanal in the presence of potassium 2-ethylhexanoate to form 2-ethylhexanoic acid with subsequent distillation which had the following composition (% by weight) determined by gas chromatography was used:

| | |
|---|---|
| First fraction | 0.5 |
| Intermediate fraction | 0.6 |
| 2-Ethylhexanoic acid | 96.2 |
| Final fraction | 2.7 |
| Potassium content (% by weight) based on the distillation residue | 8.7 |

The treatment of the potassium-containing residue from the preparation and distillation of 2-ethylhexanoic acid was carried out using the experimental setup shown in principle in FIG. 1. The distillation residue which had been heated to 50° C. was supplied via line (1) and a 5% strength by weight aqueous sulphuric acid which had likewise been heated to 50° C. was supplied via line (2). The two liquids were combined in line (3) and intensively mixed in the static mixer (4), Sulzer mixer model SMX DN4. The two-phase mixture was conveyed via line (5) to the bottom of a vertical packed column having a length of 20 cm and a 250 ml bed of 2 mm V2A helices. The two-phase mixture taken off via line (7) at the top of the reactor went into the phase separator (8) in which a spontaneous phase separation with sharp phase interfaces occurred within a few seconds. The crude 2-ethylhexanoic acid liberated was discharged via line (10) and the lower, aqueous phase containing excess sulphuric acid and potassium hydrogen sulphate/potassium sulphate was discharged via line (11) and gaseous components were discharged via line (9).

Table 1 below shows the results from different pH settings. It can be seen here that, after phase separation, there is a correlation between the pH and the potassium content in the organic phase, so that the potassium content in the organic phase can be concluded from the simple-to-carry out pH measurement. The pH measurement was carried out using a model CG836 pH meter from Schott.

TABLE 1

Reaction of the distillation residues from the preparation of 2-ethylhexanoic acid with 5% strength, aqueous sulphuric acid in the tube reactor

| Experiment | pH of org. phase | pH of aq. phase | Potassium content of org. phase (%) (*) | Ratio of org./aq. phase | V/Vh (1/h) (**) |
|---|---|---|---|---|---|
| 1 | 6.5 | 6.3 | 1.8 | 1.58 | n.d. |
| 2 | 5.9 | 4.8 | 1.4 | 0.52 | 1.7 |
| 3 | 5.7 | 2.9 | 0.67 | 0.74 | n.d. |
| 4 | 5.1 | 0.8 | 0.08 | 0.39 | n.d. |
| 5 | 4.7 | 1.2 | 0.04 | 0.32 | n.d. |
| 6 | 4.3 | 1.3 | b.d.l. | 0.28 | 1.4 |
| 7 | 4.1 | 1.0 | b.d.l. | 0.17 | 1.6 |
| 8 | 2.6 | 1.3 | b.d.l. | 0.23 | 1.5 |

(*) b.d.l. = below the detection limit;
(**) n.d. = not determined

As the results from Experiments 5 and 6 show, the pH in the organic phase should be less than 4.5 in order to ensure a sufficiently high removal of potassium. The potassium content was determined by titration of the potassium 2-ethylhexanoate with hydrochloric acid and conversion to potassium with a detection limit of 100 ppm. If the pH of the aqueous phase is employed as a guide for the potassium content in the organic phase, a pH of less 1.3 should be set.

Reuse of the Aqueous Phase:

The experimental conditions of Experiment 7 were modified by recirculating the aqueous, acidic solution separated off in the phase separator (8) via lines (11') and (2') without addition of fresh acid to the neutralization process. The results are shown in Table 2 below.

TABLE 2

Reuse of the aqueous phase for the reaction of the distillation residues from the preparation of 2-ethylhexanoic acid

| Experiment | pH of org. phase | pH of aq. phase | Potassium content of org. phase (%) | Ratio of org./aq. phase | V/Vh (1/h) |
|---|---|---|---|---|---|
| 7 | 4.1 | 1.0 | b.d.l. | 0.17 | 1.6 |
| 7(a) | 4.3 | 1.1 | b.d.l. | 0.22 | 1.6 |

The reuse in experiment 7(a), too, demonstrates that the pH data for the organic phase can be used to conclude the potassium content in the organic phase.

Variation of the space velocity through the reactor: In the following experiments, the volume of the packed column was reduced the space velocity through it was thus increased. A packed column having a length of 40 cm and a diameter of 10 mm containing 2 mm V2A helices as bed having a fill height of 30 cm was used.

TABLE 3

Reaction of the distillation residues from the preparation of 2-ethylhexanoic acid with 5% strength, aqueous sulphuric acid in the tube reactor with variation of the space velocity

| Experiment | pH of org. phase | pH of aq. phase | Potassium content of org. phase (%) | Ratio of org./aq. phase | V/Vh (1/h) |
|---|---|---|---|---|---|
| 9 | 5.0 | 0.9 | 0.22 | 0.36 | 27 |
| 10 | 4.9 | 1.6 | 0.22 | 0.41 | 21 |
| 11 | 3.2 | 0.2 | 0.06 | 0.26 | 29 |

Experiments 9 to 11, too, demonstrate that the pH in the organic phase allows the potassium content to be directly concluded. If the pH in the organic phase is reduced sufficiently, satisfactory removal of potassium from the organic phase is achieved even at a high space velocity through the reactor.

Recovery of 2-methylbutyric Acid

A potassium-containing distillation residue from the oxidation of 2-methylbutanal in the presence of potassium 2-methylbutanoate to form 2-methylbutyric acid with subsequent distillation which had the following composition (% by weight) determined by gas chromatography was used:

| | |
|---|---|
| First fraction | 0.7 |
| 2-Methylbutyric acid | 62.6 |
| Final fraction | 36.7 |

-continued

| | |
|---|---|
| Potassium content (% by weight) based on the distillation residue | 4.1 |

The treatment of the potassium-containing residue from the preparation and distillation of 2-methylbutyric acid was carried out using the experimental setup shown in principle in FIG. 1. The distillation residue was supplied via line (1) and a 5% strength by weight aqueous sulphuric acid was supplied via line (2). The two liquids were combined in line 3 and intensively mixed in the static mixer (4), Sulzer mixer model SMX DN4. The two-phase mixture was conveyed via line (5) to the bottom of a vertical packed column having a length of 40 cm and a diameter of 10 mm and containing 2 mm V2A helices as bed having a fill height of 30 cm. The two-phase mixture taken off via line (7) at the top of the reactor went into the phase separator (8) in which spontaneous phase separation with sharp phase interfaces occurred within a few seconds. The crude 2-methylbutyric acid liberated was discharged via line (10) and the lower, aqueous phase containing excess sulphuric acid and potassium hydrogensulphate/potassium sulphate was discharged via line (11) and gaseous components were discharged via line (9).

Table 4 below shows the results from different pH settings. It can be seen here that, after phase separation, there is a correlation between the pH and the potassium content in the organic phase, so that the potassium content in the organic phase can be concluded from the simple-to-carry out pH measurement. The pH measurement was carried out using a model CG836 pH meter from Schott.

TABLE 4

Reaction of the distillation residues from the preparation of 2-methylbutyric acid with 5% strength, aqueous sulphuric acid in the tube reactor

| Experiment | pH of org. phase | pH of aq. phase | Potassium content of org. phase (%) | Ratio of org./aq. phase | V/Vh (1/h) |
|---|---|---|---|---|---|
| 12 | 4.2 | 2.9 | 0.44 | 0.96 | 16 |
| 13 | 2.6 | 1.6 | 0.05 | 1.12 | 23 |
| 14 | 2.5 | 1.3 | 0.03 | 0.66 | 18 |
| 15 | 2.6 | 1.0 | 0.01 | 0.50 | 18 |

As the results from Experiments 12 and 13 show, the pH in the organic phase should be less than 4.0 in order to ensure a sufficiently high removal of potassium. The potassium content was determined by titration of the potassium 2-methylbutanoate with hydrochloric acid and conversion to potassium with a detection limit of 100 ppm. If the pH of the aqueous phase is employed as a guide for the potassium content in the organic phase, a pH of less than 1.6 should be set.

Reuse of the Aqueous Phase:

The experimental condition of Experiment 14 was modified by recirculating the aqueous, acidic solution separated off in the phase separator (8) via lines (11') and (2') without addition of fresh acid to the neutralization process. The results are shown in Table 5 below.

TABLE 5

Reuse of the aqueous phase for the reaction of the distillation residues from the preparation of 2-methylbutyric acid

| Experiment | pH of org. phase | pH of aq. phase | Potassium content of org. phase (%) | Ratio of org./aq. phase | V/Vh (1/h) |
|---|---|---|---|---|---|
| 14 | 2.5 | 1.3 | 0.03 | 0.66 | 18 |
| 14(a) | 3.6 | 1.9 | 0.25 | 0.43 | 17 |
| 14(b) | 4.6 | 4.8 | 1.4 | 0.84 | 20 |

The reuse in Experiments 14(a) and 14(b), too, demonstrates that the pH data for the organic phase can be used to conclude the potassium content in the organic phase.

The invention claimed is:

1. A process for recovering aliphatic monocarboxylic acids having from 4 to 11 carbon atoms from the distillation residue obtained in the oxidation of the corresponding aldehyde by means of oxygen or oxygen-containing gas mixtures in the presence of alkali metal carboxylates or alkaline earth metal carboxylates to form the corresponding monocarboxylic acid and subsequent distillation, characterized in that the distillation residue is reacted with an aqueous acid in a tube reactor and the two-phase mixture flowing out from the tube reactor is introduced into a settling vessel in which the organic phase which separates out has a pH of 4.5 or less.

2. The process according to claim 1, characterized in that a static mixing element is installed upstream of the tube reactor.

3. The process according to claim 1, characterized in that the tube reactor contains packing elements or internals.

4. The process according to claim 1, characterized in that the distillation residue is preheated to a temperature of from 30 to 90° C.

5. The process according to claim 1, characterized in that the reaction is carried out at a temperature of from 30 to 90° C.

6. The process according to claim 1, characterized in that an aqueous solution of an inorganic acid is used as aqueous acid.

7. The process according to claim 6, characterized in that hydrochloric acid, sulphuric acid, phosphoric acid or nitric acid is used as inorganic acid.

8. The process according to claim 1, characterized in that the distillation residues from the preparation of aliphatic straight-chain or branched monocarboxylic acids are used.

9. The process according to claim 8, characterized in that the distillation residues from the preparation of aliphatic straight-chain monocarboxylic acids selected from the group consisting of n-butyric acid, n-pentanoic acid, n-hexanoic acid, n-heptanoic acid, n-octanoic acid, n-nonanoic acid and n-decanoic acid are used.

10. The process according to claim 8, characterized in that the distillation residues from the preparation of aliphatic, α-alkyl-branched monocarboxylic acids are used.

11. The process according to claim 10, characterized in that isobutyric acid, 2-ethylbutyric acid, 2-methylbutyric acid, 2-methylpentanoic acid, 2-methylhexanoic acid, 2-ethylhexanoic acid, 2-methyloctanoic acid, 2-methylnonanoic acid, 2-propylheptanoic acid, 2-ethylbutenoic acid, 2-methylpentenoic acid, 2-ethylhexenoic acid or 2-propylheptenoic acid is used as aliphatic, α-alkyl-branched monocarboxylic acid.

12. The process according to claim 8, characterized in that the distillation residues from the preparation of aliphatic branched monocarboxylic acids which are not α-alkyl-branched are used.

13. The process according to claim 12, characterized in that an isopentanoic acid having any branching, isohexanoic acid having any branching, isoheptanoic acid having any branching, isooctanoic acid having any branching, isononanoic acid having any branching, isodecanoic acid having any branching or isoundecanoic acid having any branching is used as aliphatic branched monocarboxylic acid, with the proviso that there is no α-alkyl branching.

14. The process according to claim 13, characterized in that 3-methylbutyric acid is used as isopentanoic acid having any branching.

15. The process according to claim 13, characterized in that an isononanoic acid having the main constituent 3,5,5-trimethylhexanoic acid is used as isononanoic acid having any branching.

16. The process according to one or more of claim 1, characterized in that the potassium carboxylate- or sodium carboxylate-containing distillation residues of the corresponding monocarboxylic acids are reacted with the aqueous acid.

17. The process according to claim 1, characterized in that the distillation residue is preheated to a temperature of from 50 to 80° C.

18. The process according to claim 1, characterized in that the reaction is carried out at a temperature of from 50 to 80° C.

19. The process according to claim 5, characterized in that an aqueous solution of an inorganic acid is used as aqueous acid.

20. The process according to claim 19, characterized in that hydrochloric acid, sulphuric acid, phosphoric acid or nitric acid is used as inorganic acid.

* * * * *